United States Patent [19]
Lin

[11] Patent Number: 5,403,313
[45] Date of Patent: Apr. 4, 1995

[54] EXTERNAL FIXATION DEVICE FOR FRACTURED BONE

[76] Inventor: Chih-I Lin, 513 S. Golden Pardos Dr., Diamond Bar, Calif. 10765

[21] Appl. No.: 98,868

[22] Filed: Jul. 29, 1993

[51] Int. Cl.[6] .............................................. A61B 17/60
[52] U.S. Cl. ........................................ 606/54; 606/59
[58] Field of Search ................ 606/59, 54, 57, 72, 606/73

[56] References Cited

U.S. PATENT DOCUMENTS 2,333,033 10/1943 Mraz ..................................... 606/57

FOREIGN PATENT DOCUMENTS 789882 11/1935 France .................................. 606/59
2164859 4/1986 United Kingdom ................. 606/59
WO90/11727 10/1990 WIPO .................................... 606/57
91/05516 5/1991 WIPO .................................... 606/54

*Primary Examiner*—Tamara L. Graysay
*Attorney, Agent, or Firm*—Bacon & Thomas

[57] ABSTRACT

An external fixation device for a fractured bone comprises a fixation rod, a connection member, and a plurality of fixing screws. The connection member has one end serving as a clamp to hold firmly the fixation rod and another end serving as a screw receiving mount provided with a plurality of clamping holes which are neither aligned nor parallel to one another. The fixing screws are fastened respectively onto a bone through the clamping holes in a specified angle.

4 Claims, 4 Drawing Sheets

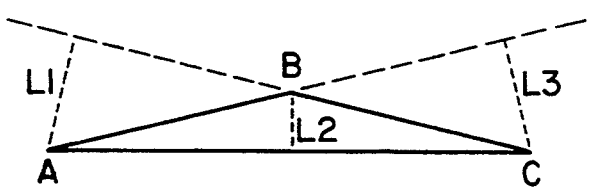
FIG. 1d
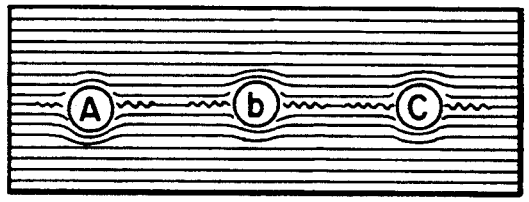
FIG. 1e
(PRIOR ART)
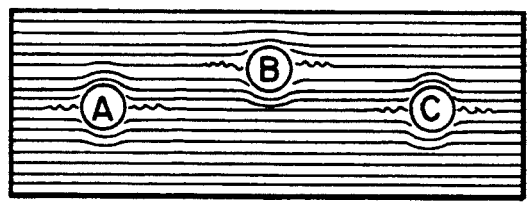
FIG. 1f
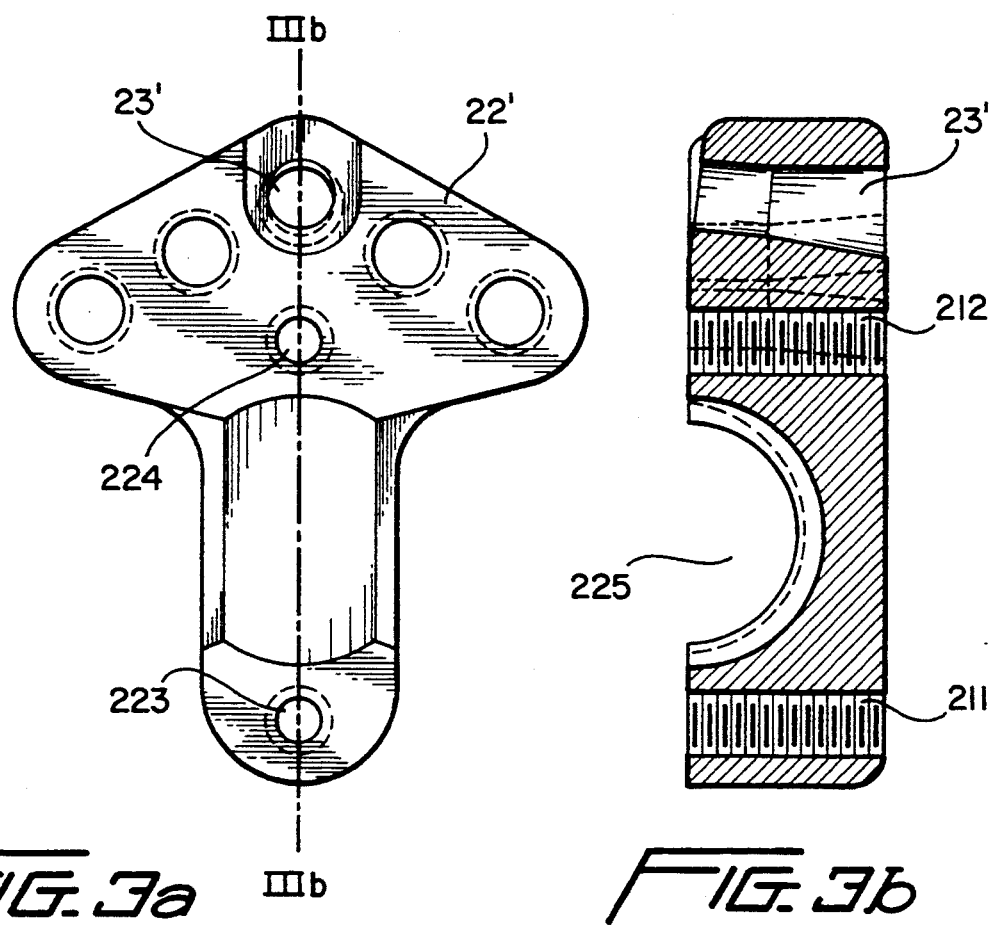
FIG. 3a
FIG. 3b

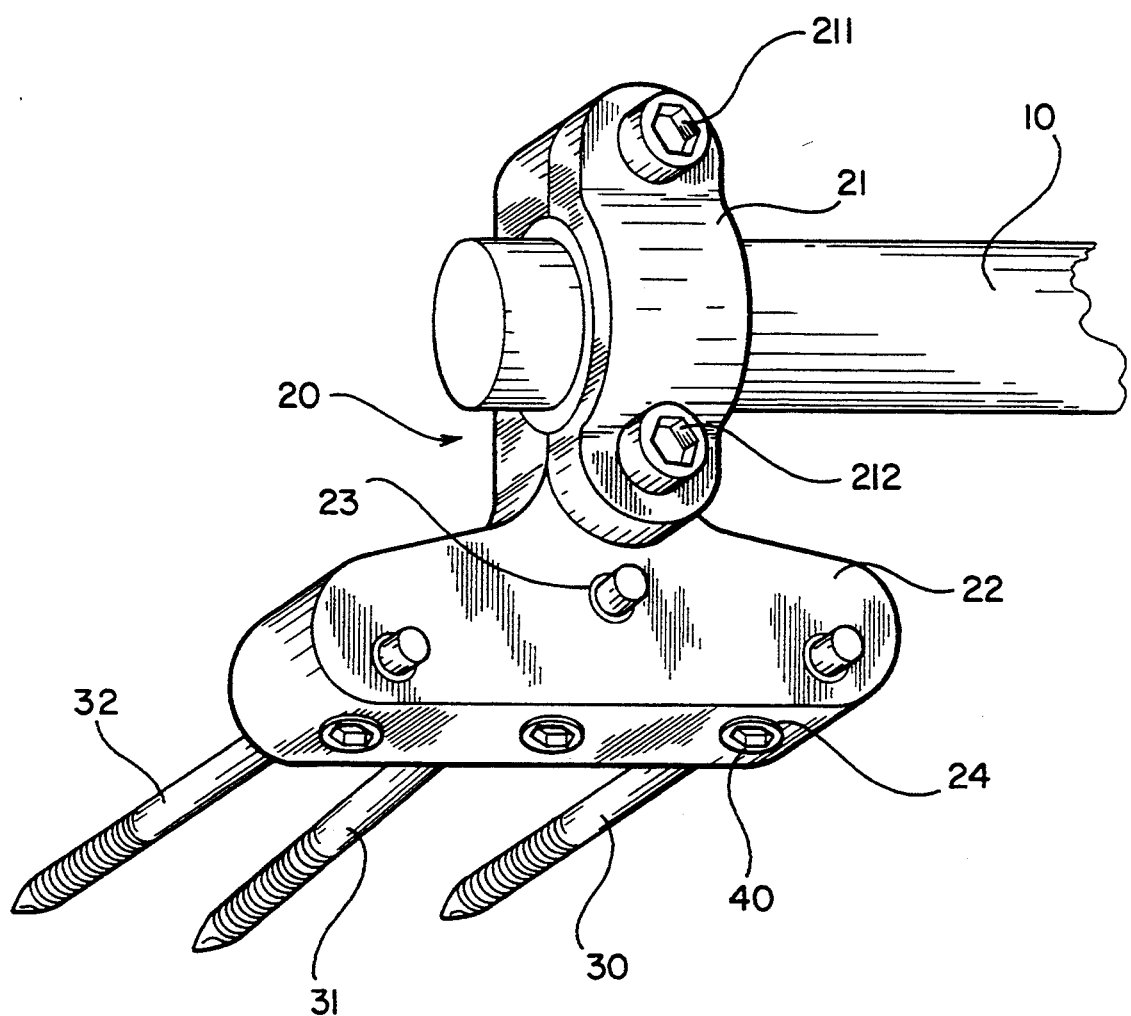

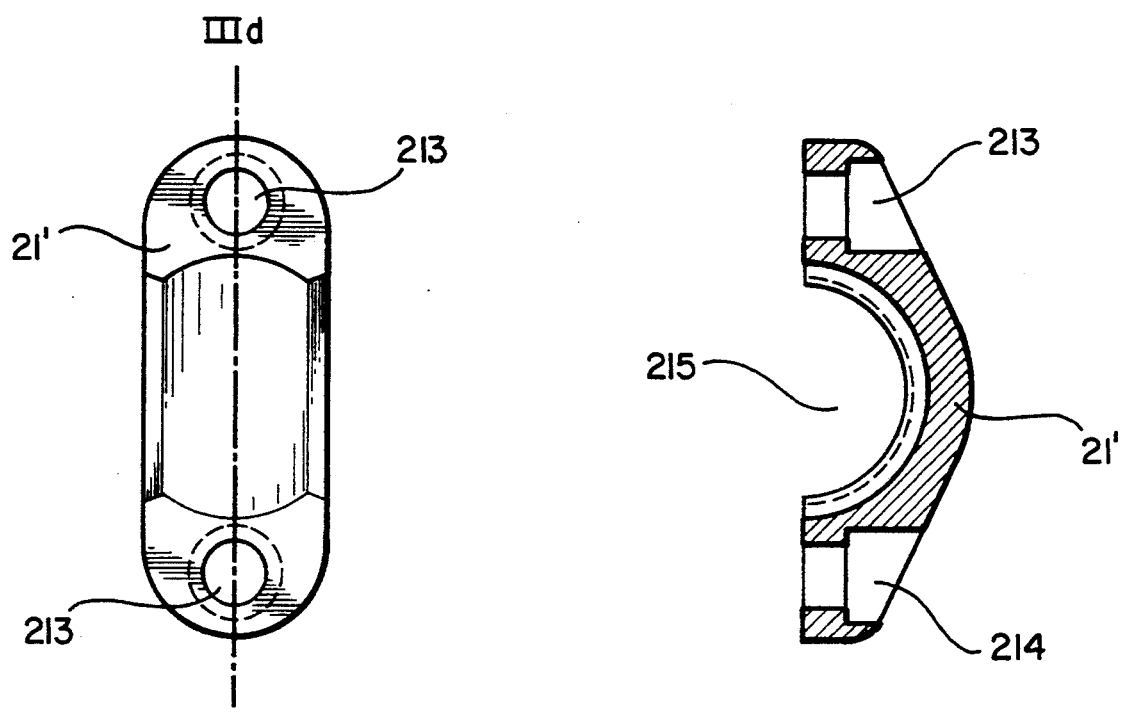
FIG. 3c
FIG. 3d
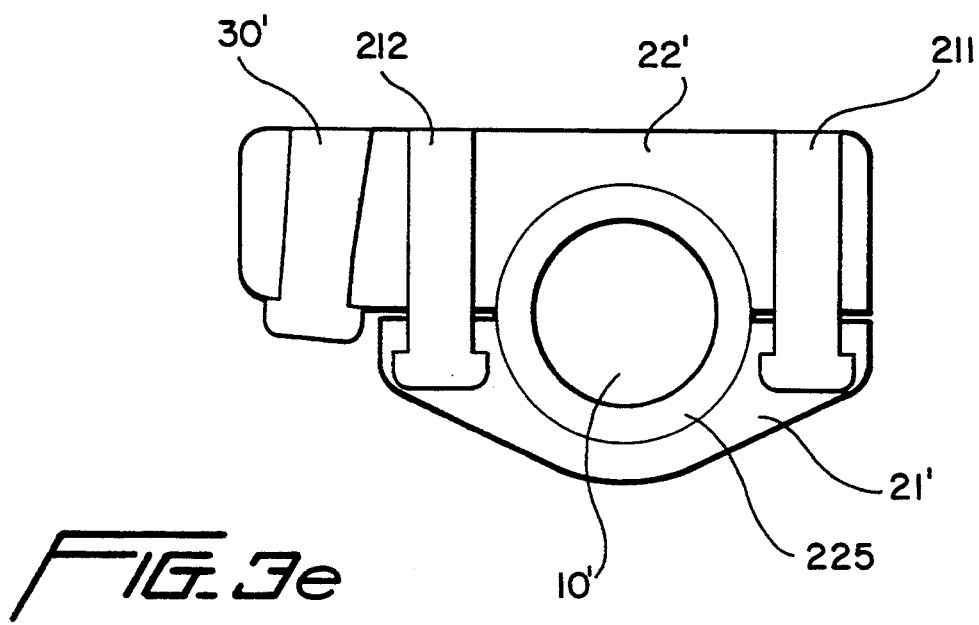
FIG. 3e

EXTERNAL FIXATION DEVICE FOR FRACTURED BONE

FIELD OF THE INVENTION

The present invention relates to an external fixation device for a fractured bone.

BACKGROUND OF THE INVENTION

There are various external methods of fixing a fractured bone, such as the radial external fixation system, the femoral standard frame and the tibial standard lengthening frame which are made by the Daruma Corporation of the United States. Such conventional methods as mentioned above are defective in design in that they are complicated in construction and that they hamper the mobility of a patient under treatment. For this reason, the orthopedic surgeons are more inclined to make use of monotube fixation devices, such as the articulated components introduced by EBI Medical Systems, Inc. of the United States, and the external fixation system made by the Howmedica Corporation of the United States and sold under the trademark Mono-tube TM. These monotube fixation systems involve the use of a clamping structure to hold firmly the bone screws which are fastened onto the bone. As shown in FIG. 1a, the clamping holes A, b and C are aligned while the screws AA', bE' and CC' are so oriented that they are in the same plane designated by ACC'A' and that they are parallel to one another. As a result, the fixing effect on the bone of such monotube fixation systems as described above is generally unsatisfactory, to say the least.

SUMMARY OF THE INVENTION

It is therefore the primary objective of the present invention to provide an external fixation device which comprises a plurality of bone screws that are fastened respectively at a specified angle onto a bone intended to be fixed.

It is another objective of the present invention to provide an external fixation device which is composed of a connection member provided with a plurality of clamping holes that are not aligned and are oriented respectively at a specified angle.

It is still another objective of the present invention to provide an external fixation device with a connection member and a fixation rod, which are fastened securely by means of a universal locking system.

In keeping with the principle of the present invention, the foregoing objectives of the present invention are attained by an external fixation device, which comprises a fixation rod, a connection member and a plurality of bone screws. The connection member has one end holding securely the fixation rod and another end serving as a screw receiving mount provided with a plurality of clamping holes through which the bone screws are fastened onto a bone intended to be fixed. The clamping holes are such that they are not aligned and that they are oriented respectively at a specified angle so as to permit the bone screws to be fastened respectively onto the bone at a specified angle.

BRIEF DESCRIPTION OF THE DRAWINGS

FIG. 1d schematically illustrates the force distribution associated with the external fixation device of the present invention;

FIG. 1e illustrates the arrangement of fixing screws to a connection member in accordance with the prior art;

FIG. 1f illustrates the arrangement of fixing screws to a connection member in accordance with the present invention;

FIG. 2 is a perspective view of a portion of the external fixation device according to a first embodiment of the present invention;

FIG. 3a is a top view of a connection member in accordance with a second preferred embodiment of the external fixation device of the present invention;

FIG. 3b is a cross-sectional view generally taken along IIIb-IIIb of the connection member of FIG. 3a;

FIG. 3c is a top view of another portion of the connection member incorporated in the second preferred embodiment of the external fixation device of the present invention;

FIG. 3d is a cross-sectional view generally taken along line IIId—IIId of FIG. 3c; and FIG. 3e schematically illustrates the second preferred embodiment of the external fixation device of the present invention in its assembled state.

DETAILED DESCRIPTION OF THE INVENTION

Figure 1A:
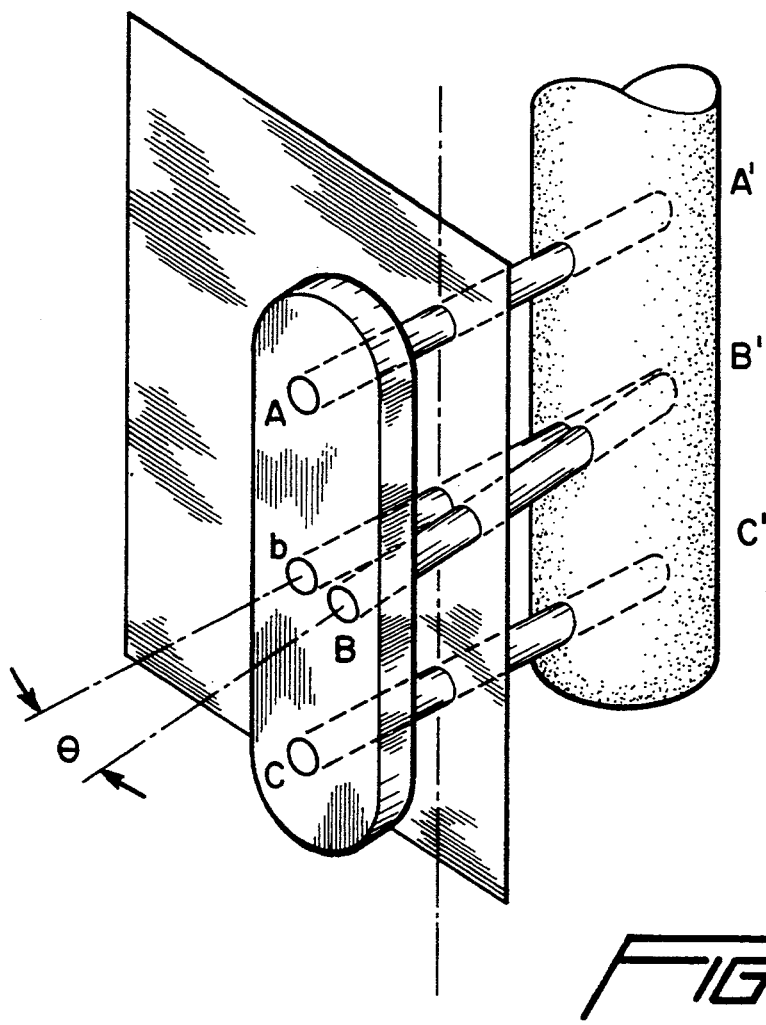
FIG. 1a depicts the external. fixation device of the present invention as compared to the prior art.

Referring to FIG. 2, an external fixation device of a first preferred embodiment of the present invention is shown to comprise a fixation rod 10, a connection member 20, and a plurality of fixing screws 30, 31 and 32. The connection member 20 is provided with a clamp 21, a screw-receiving mount 22, and a plurality of clamping holes 23 and auxiliary threaded holes 24. The clamp 21 is provided with two bolts 211 and 212 by means of which the clamp 21 is fastened to the screw-receiving mount 22. The fixing screws 30, 31 and 32 are held securely in place by means of three auxiliary bolts 40 engageable respectively with the three auxiliary threaded holes 24. As shown clearly in FIG. 2, the three clamping holes 23 of the connection member 20 of the present invention are not aligned. In addition, the three fixing screws 30, 31 and 32 are fastened onto a bone (not shown in the drawing) such that they are not parallel to one another.

Another embodiment of the present invention is illustrated in FIGS. 3a–3e and is shown to comprise a fixation rod 10' a screw-receiving mount 22' a clamp 21' and fixing screws 30'. The screw-receiving mount 22' is provided with two threaded holes 223 and 224, which are corresponding in location to the two threaded holes 213 and 214 of the clamp 21'. The screw-receiving mount 22' is provided with five clamping holes 23' through which the fixing screws 30' are fastened respectively onto a bone (not shown in the drawing). FIG. 3b is a sectional view of a portion taken along the line IIIb—IIIb as shown in FIG. 3a. The screw receiving mount 22' is shown comprising a slot 225 intended to accommodate the fixation rod 10. FIG. 3d is a sectional view of a portion taken along the line IIId—IIId as shown in FIG. 3c. The clamp 21 is shown in FIG. 3d to comprise a slot 215 to receive therein the fixation rod 10 and two threaded holes 213 and 214. It must be noted here that the screw-receiving mount 22′ comprises two bolts 211 and 212 and two threaded holes 223 and 224, as shown respectively in FIGS. 3a and 3b. The fixation rod 10′ the clamp 21′ and the screw-receiving mount 22′ are fastened together by means of two bolts 211 and 212, as shown in FIG. 3e in which only one of a plurality of the fixing screws 30′ is shown. The fixing screws 30′ are fastened onto a bone (not shown in the drawing).

The fixation rod 10, 10′ the connection member 20, 20′ and the clamp 21, 21′ are respectively fastened together by any fastening method known in the art. For example, the fixation rod 10, 10′ may be held securely in place by means of two arcuate clamping pieces which are in turn tightened by means of screws as outlined above. Another suggested method is the V-groove connecting design sold by the DANEK Corporation of the United States under the trademark SOLA. However, the fastening methods described above are limited in that the fixation rod 10, 10′ and the connection member 20, 10′ can be adjusted only unidirectionally. For this reason, this invention discloses a universal fixation system, which permits the fixation rod and the connection member to be adjusted in any direction as desired.

The screw-receiving mount 22, 22′ of the connection member 20, 20′ respectively of the present invention may be made up of a set of clamping tools having the clamping holes that are located at a place where the clamping tools are braced together. The screw-receiving mount may be made up of structure similar to that of the monotube external fixation device of the prior art. It is suggested that the latter is used so as to prevent the clamping tools from becoming loosened.

The most improtant feature of the present invention is that the clamping holes 23, 23′ of the screw-receiving mount 22, 22′ respectively are not situated in the same plane, and that each of the clamping holes 23, 23′ is oriented at a specified angle $\theta$ in relation to other clamping holes 23, 23′ with the specified angle $\theta$ being greater than zero degree and smaller than 30 degrees. As a result, the tensile strength, the shearing strength, the bending strength and the torque strength of the clamping holes 23, 23′ of the present invention are greatly enhanced.

Figure 1B:
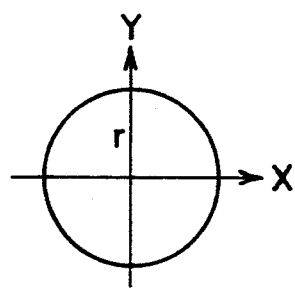
FIG. 1b is a schematic representation of the cross-sectional area of a fixation rod used in an external fixation device according to the prior art.
Figure 1C:
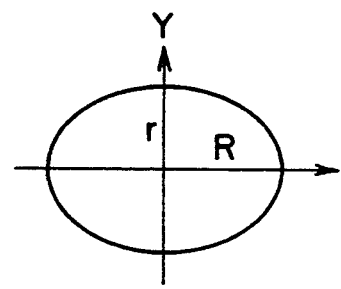
FIG. 1c is schematic representation of the cross-sectional area of a fixation rod used in an external fixation device in accordance with the present invention.

The advantages inherent in the present invention can be made further apparent by comparing the device of the present invention with that of the prior art. As illustrated in a portion of FIG. 1a, the prior art device is provided with three clamping holes A, b and C, which are so aligned that the fixing screws AA′, bB′ and CC′ passing therethrough are all situated in the same plane designated by ACC′A′. In addition, the fixing screws AA′, bB′ and CC′ are fastened onto the bone in such a manner that the fixing screws AA′, bB′ and CC′ are parallel to one another. On the other hand, the present invention is provided with the clamping holes A, B and C, which are not aligned, and with the fixing screws AA′, BB′ and CC′, which are neither in the same place ACC′A nor parallel to one another. In view of the fact that the fixing screws BB′ and bB′ form a specified angle $\theta$, such as 5 degrees of 10 degrees or 15 degrees the fixation rod 10, 10′ has an oval cross section which is greater than the cross-sectional area of the fixation rod of the prior art, as shown respectively in FIGS. 1c and 1b. Accordingly, the present invention has a relatively greater moment of inertia. Assuming that the fixing screws BB′ and bB are fastened onto the bone such that they form the angles of 5 degrees, 10 degrees and 15 degrees respectively. The relations between the moments of inertia of the cross sections B and b can be expressed respectively as IYB=1.01 IYb (5°), IYB=1.04 IYb (10°), IYB=1.1 IYb 1 (15°), in which IY stands for moment of inertia. As a result, the present invention is superior to the prior aft in terms of tensile strength, shearing strength, bending strength and torque strength.

Moreover, when the points A, b and C of the prior art are exerted on by a fOrCe, only AC bears the burden of the force (Ab+bC=AC). On the other hand, when the points A, B and C of the present invention are similarly exerted on by the same force as mentioned above, AB, AC and BC share the burden of the force. This means that each of AB, AC and BC is exerted on by a smaller force and that the burden of the force is shared effectively by the three moments designated as IL1, L2 and L3 in FIG. 1d.

Now referring to FIGS. 1e and 1f, the connection member of the prior art device is shown to comprise the points A, b and C, which are so aligned that the connection member is bound to break between the points A and b or between the points b and C. On the contrary, the points A, B and C of the connecton member of the present invention are not aligned such that the connection member is less vulnerable to the breakage.

As described previously, the most important features of the present invention includes the noncoplanar arrangement of the clamping holes 23, 23′ of the screw-receiving mount 22, 22′ respectively, the angled arrangement of the clamping holes 23, 23′, and the nonparallel arrangement of the clamping holes 23, 23′. It must be noted here that the clamping holes of the screw-receiving mount of the present invention may be replaced with the clamping holes of the conventional clamping tools or with the clamping holes of the monoplate screw-receiving mount, preferably the latter. In order to reinforce the fastening of the fixing screws to the screw-receiving mount, an auxiliary fixing device, such as the lateral screw, may be employed.

The fixing screws of the present invention are similar in structure and function to the fixing screws of the prior art. However, it is suggested that the fixing screws of the present invention be insulated from the connection member by an insulating sheath or a coating of the insulating material.

Any auxiliary system of the prior art may be employed to reinforce the fixing effect of the present invention.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

I claim:

1. An external fixation device for use in stabilizing a fractured bone comprising:
   a fixation rod;
   a connection member having a first portion securely attached to said fixation rod and a second portion defining a screw receiving mount, said screw receiving mount being provided with at least three clamping holes extending therethrough, two of said at least three clamping holes extending through said connection member parallel to each other in a common plane, a third of said at least three clamping holes extending through said connection member at a specified angle to said common plane; and a plurality of fixing screws, each one of said fixing screws extending through a respective one of said clamping holes and being adapted to be fastened to a bone.

2. The external fixation device of claim 1, wherein said specified angle is greater than zero degrees and less than 30 degrees.

3. The external fixation device of claim 2, wherein the second portion of said connection member through which said clamping holes extend comprises a single plate.

4. The external fixation device of claim 3, wherein the first portion of said connection member comprises a clamp for securing said connection member to said fixation rod.

* * * * *